United States Patent [19]

Kimura et al.

[11] Patent Number: 5,472,483

[45] Date of Patent: Dec. 5, 1995

[54] ANTIFOULING AGENT

[75] Inventors: Ryoji Kimura; Mitsuhiro Hamajima, both of Tokyo, Japan

[73] Assignee: Asahi Denka Kogyo Kabushiki Kaisha, Tokyo, Japan

[21] Appl. No.: 344,584

[22] Filed: Nov. 18, 1994

[51] Int. Cl.$^6$ .............. C09D 5/14; A01N 31/00
[52] U.S. Cl. ............. 106/18.34; 106/18.33; 424/78.09; 514/706; 514/707; 523/122
[58] Field of Search ............... 106/18.33, 18.34, 106/18.35; 424/78.09; 523/122; 514/706, 707

[56] References Cited

U.S. PATENT DOCUMENTS

| | | | |
|---|---|---|---|
| 3,138,519 | 6/1964 | Riden, Jr. et al. | 106/18.34 |
| 3,409,724 | 11/1968 | Magee | 106/18.33 |
| 4,295,887 | 10/1981 | Buckley et al. | 106/18.34 |
| 4,298,384 | 11/1981 | Allingham et al. | 106/18.34 |
| 4,331,480 | 5/1982 | Gutman et al. | 106/18.33 |
| 5,125,967 | 6/1992 | Morpeth et al. | 106/18.34 |

FOREIGN PATENT DOCUMENTS

| | | | |
|---|---|---|---|
| 2309241 | 11/1976 | France | 106/18.33 |
| 2615662 | 10/1976 | Germany | 106/18.33 |
| 2810698 | 9/1979 | Germany . | |
| 56-034604 | 4/1981 | Japan . | |
| 2234250 | 1/1991 | United Kingdom . | |

OTHER PUBLICATIONS

Bando, K., et al., "Insecticidal, Acaricidal, and Fungicidal Activities of Disulfide Compounds", *Chemical Abstracts*, vol. 69, No. 19, 1968, Abstract No. 75902d, p. 7079 no month.

*Primary Examiner*—Anthony Green
*Attorney, Agent, or Firm*—Young & Thompson

[57] ABSTRACT

An antifouling agent containing, as an active ingredient, one or more compounds represented by formula (I):

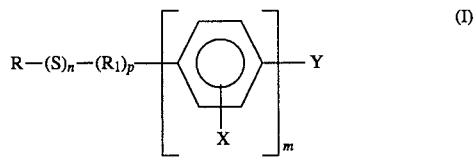

wherein R represents an alkyl group; $R_1$ represents an alkylene group; n represents an integer of 2 to 5; m and p each represent 0 or 1; X represents a nitro group, an alkyl group, an alkoxy group, a halogen atom or a hydrogen atom; and Y represents a nitro group or a halogen atom; provided that the sum of m and p is 1 or 2.

14 Claims, No Drawings

ANTIFOULING AGENT

FIELD OF THE INVENTION

This invention relates to an antifouling agent for protecting submerged structures against damages due to adhesion and propagation of aquatic pests in sea water or industrial water systems. More particularly, it relates to an antifouling agent which can be used for preventing aquatic pests from adhering to the surface of submerged structures, such as ships, fishing nets, buoys, and sea water guide pipes.

BACKGROUND OF THE INVENTION

Submerged structures, such as ships, port facilities, buoys, pipe lines, bridges, excavators for seabed oil fields, water pipes in electric power plants or seaside plants, fishing nets, and rafts for aquaculture, suffer from adhesion of relatively large animals and plants, such as barnacles, hard-shelled mussels and lavers, and microorganisms, such as diatoms and bacteria, which leads to various damages, for example, corrosion of the structures, increase in sea water friction of ships, mass death of fishes due to jamming of the fishing net, sinking of structures due to weight gain, and reduction in working efficiency. In industrial water systems using natural water from rivers and lakes as, for example cooling water or in circulating cooling systems using moderately or highly purified city water, abnormal propagation of bacteria, diatoms, blue-green algae, spirogyra, etc. causes various troubles, such as deterioration of water qualities, reduction in cooling efficiency, obstruction of pipes, and reduction in flow rate.

In order to prevent these troubles caused by aquatic pests, it has been a practice to apply antifouling agents containing inorganic heavy metal compounds, such as copper suboxide, copper rhodanide, and mercury oxide, or organic metal compounds, such as tributyltin oxide, triphenyltin oxide, and tributyltin (meth)acrylate polymers.

However, these compounds which have been conventionally employed for the above-mentioned purpose are highly toxic, not only needing special care in handling but resulting in environmental pollution, including malformation of fishes due to accumulation in fish bodies. It has therefore been demanded to use an antifouling agent containing no heavy metals or organic metals.

Various compounds containing sulfur, such as thiuram compounds, benzothiazole compounds and thiocyanogen compounds, have been proposed as antifouling agents free from any heavy metal or organic metal, but their effects are still insufficient. A combined use of a dialkyl polysulfide compound with another pesticidal compound as an antifouling agent for fishing nets has been proposed as disclosed in Japanese Patent Laid-Open No. 38306/85. However, as the publication mentions, the dialkyl polysulfide compound per se has no biological activity.

SUMMARY OF THE INVENTION

Accordingly, an object of the present invention is to provide an antifouling agent for use in water, which gives rise to no safety, hygienic or environmental problems, that is, having low toxicity and low retentivity in bodies and exerting its effects over a long period of time without adversely affecting the ecosystem or the working environment.

The present inventors have conducted extensive studies and, as a result, found that the above object of the present invention is accomplished by an antifouling agent containing a specific polysulfide compound. The present invention has been completed based on this finding.

The present invention provides an antifouling agent containing, as an active ingredient, one or more compounds represented by formula (I):

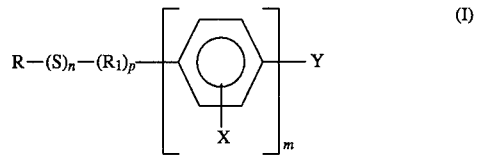

wherein R represents an alkyl group; $R_1$ represents an alkylene group; n represents an integer of 2 to 5; m and p each represent 0 or 1; X represents a nitro group, an alkyl group, an alkoxy group, a halogen atom or a hydrogen atom; and Y represents a nitro group or a halogen atom; provided that the sum of m and p is 1 or 2.

The antifouling agent according to the present invention gives rise to no safety, hygienic or environmental problems. That is, it has low toxicity and low retentivity in bodies and exerts its effects over a long period of time without adversely affecting the ecosystem or the working environment.

DETAILED DESCRIPTION OF THE INVENTION

In formula (I), the alkyl group represented by R includes straight-chain or branched alkyl groups, such as methyl, ethyl, propyl, isopropyl, butyl, isobutyl, sec-butyl, t-butyl, amyl, hexyl, heptyl, octyl, isooctyl, 2-ethylhexyl, t-octyl, nonyl, isononyl, t-nonyl, decyl, isodecyl, dodecyl, tridecyl, isotridecyl, tetradecyl, hexadecyl, octadecyl, eicosyl, docosyl, tetracosyl, and triacontyl groups. Preferably, the alkyl group represented by R has 6 to 18 carbon atoms. The alkylene group as represented by $R_1$ includes methylene, ethylene, propylene and butylene groups, and preferably has 1 to 4 carbon atoms. The alkyl group as represented by X includes methyl, ethyl, propyl, isopropyl, butyl, isobutyl, sec-butyl, and t-butyl groups. The alkoxy group as represented by X includes methoxy, ethoxy, propoxy, and butoxy groups. The halogen atom as represented by X or Y includes fluorine, chlorine, bromine, and iodine.

Specific examples of the compound represented by formula (I) include Compounds 1 to 14 shown below:

Compound 1: n-$C_8H_{17}$—S—S—$CH_2Cl$
Compound 2: iso-$C_8H_{17}$—S—S—$CH_2Cl$
Compound 3: n-$C_{12}H_{25}$—S—S—$CH_2Cl$
Compound 4: n-$C_{18}H_{37}$—S—S—$CH_2Cl$
Compound 5: n-$C_8H_{17}$—$S_3$—$CH_2Cl$
Compound 6: n-$C_8H_{17}$—S—S—$CH_2Br$
Compound 7: n-$C_8H_{17}$—S—S—$CH_2NO_2$

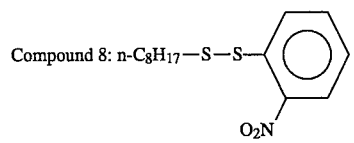

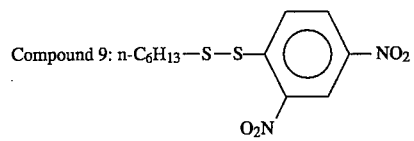

-continued

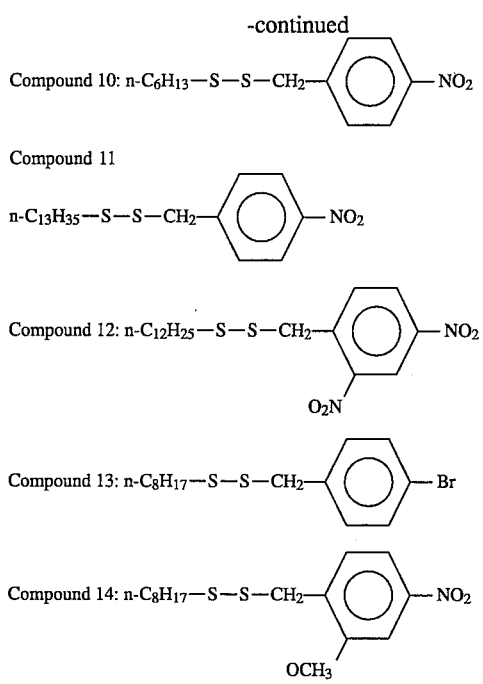

Compound 10: n-C₆H₁₃—S—S—CH₂—⟨C₆H₄⟩—NO₂

Compound 11: n-C₁₃H₃₅—S—S—CH₂—⟨C₆H₄⟩—NO₂

Compound 12: n-C₁₂H₂₅—S—S—CH₂—⟨C₆H₃(O₂N)⟩—NO₂

Compound 13: n-C₈H₁₇—S—S—CH₂—⟨C₆H₄⟩—Br

Compound 14: n-C₈H₁₇—S—S—CH₂—⟨C₆H₃(OCH₃)⟩—NO₂

Some of the compounds represented by formula (I) are known compounds and can easily be prepared by, for example, reacting a thioalcohol with a halogen- or nitro-substituted alkyl/arylthiocyanate or alkyl/arylsulfonyl chloride.

Synthesis Examples for the compounds of formula (I) are described below only for illustrative purposes but not for limitation.

SYNTHESIS EXAMPLE 1

Synthesis of Compound 1 In a flask were charged 14.63 g of n-octyl thioalcohol, 10.76 g of chloromethyl thiocyanate, 20 g of acetone, and 14 g of anhydrous potassium carbonate, and the mixture was allowed to react under reflux for 5 hours. The insoluble matter formed was removed by filtration, and acetone was removed by means of an evaporator. The residue was distilled under reduced pressure to obtain a fraction of 150° C., 12 mmHg.

The IR spectrum of the product showed absorptions assigned to an alkyl group at 2940 $cm^{-1}$, 2910 $cm^{-1}$ and 2840 $cm^{-1}$ and an absorption assigned to a C—Cl bond at 700 $cm^{-1}$. The mass spectrometry gave m/z of 226. The $H^1$-NMR spectrum showed chemical shifts of 4.7 ppm (s) 2H, 2.9 ppm (t) 2H, and 2.6 to 0.6 ppm (m) 15H. These analytical results lent confirmation to the identity of the product as the desired compound.

SYNTHESIS EXAMPLE 2

Synthesis of Compound 8

In a flask 5.7 g of 2-nitrobenzenesulfonyl chloride was dissolved in 30 ml of methylene chloride, and 4.4 g of n-octyl thioalcohol was added to the solution dropwise while cooling at −5° C. After the addition, the inner temperature was gradually raised up to room temperature, at which the mixture was allowed to react for 2 hours. Methylene chloride was removed by means of an evaporator to obtain a pale yellow liquid having a melting point of 15 to 20 ° C.

The IR spectrum of the product showed absorptions assigned to an N—O bond at 1510 $cm^{-1}$ and 1470 $cm^{-1}$. The mass spectrum showed m/z=298. The $H^1$-NMR spectrum exhibited chemical shifts of 7.0 to 8.5 ppm (m) 4H, 2.8 ppm (t) 2H, and 0.5 to 2.0 ppm (m) 4H. From these analytical results, the product was identified to be the desired compound.

The present invention consists in an antifouling agent containing one or more of the compounds represented by formula (I) as an active ingredient. If desired, the antifouling agent of the present invention may contain one or more conventional antifouling agents in combination. In some cases such a combined use brings about a sustained duration of the effects.

The antifouling agents which can be used together with the compound of formula (I) include thiuram compounds, such as tetramethylthiuram disulfide, tetraethylthiuram disulfide, tetra-n-propylthiuram disulfide, tetraisopropylthiuram disulfide, tetra-n-butylthiuram disulfide, tetraisobutylthiuram disulfide, N,N'-ethylenebisthiocarbamoyl sulfide, N,N'-propylenebisthiocarbamoyl sulfide, and N,N'-butylenebisthiocarbamoyl sulfide; copper-based metal powders, such as copper powder and copper-nickel alloy powder; copper compounds, such as cuprous oxide, cuprous thiocyanate, basic copper carbonate, copper pyrophosphate, copper naphthenate, copper abietate, and copper oxyquinoline; dithiocarbamate compounds, such as zinc dimethyldithiocarbamate, zinc diethyldithiocarbamate, zinc dibutyldithiocarbamate, zinc ethylphenyldithiocarbamate, zinc ethylenebisdithiocarbamate, zinc propylenebisdithiocarbamate, zinc bis(dimethyldithiocarbamoyl)ethylenebisdithiocarbamate, manganese ethylenebisdithiocarbamate, nickel dimethyldithiocarbamate, nickel dibutyldithiocarbamate, copper dimethyldithiocarbamate, and iron dimethyldithiocarbamate; benzimidazole compounds, such as 2-(4-thiazolyl)benzimidazole, methyl-1-(ω-cyanopentylcarbamoyl)- 2-benzimidazole, zinc 2-mercaptobenzimidazole, and 2-thiocyanomethylthiobenzimidazole; benzothiazole compounds, such as 2-mercaptobenzothiazole, 2-(thiocyanomethylthio)benzothiazole, 2-(thiocyanomethylsulfonyl)benzothiazole, 2-thiocyanoethylthio-4-chlorobenzothiazole, 2-thiocyanopropylthio-5,7-dichlorobenzothiazole, and 2-thiocyanomethylthio-4,5,6,7-tetrachlorobenzothiazole; nitrile compounds, such as tetrachloroisophthalonitrile and 5-chloro-2,4-difluoro-6-methoxyisophthalonitrile; isothiazoline compounds, such as 4,5-dichloro-2-n-octyl-4-isothiazolin-3-one, 2-n-octyl-4-isothiazolin-3-one, and 1,2-benzoisothiazolin- 3-one; triazole compounds, such as 1-[2-(2,4-dichlorophenyl)- 4-propyl-1,3-dioxolanyl-2-methyl]-1H- 1,2,4-triazole and 4,4-dimethyl-2-(1,2,4-triazol-1-yl)- 1-(4-trifluoromethyl-2-chlorophenyl)-1-penten-2-ol; pyridine compounds, such as 2,3,5,6-tetrachloro-4-(methylsulfonyl)pyridine, 2,3,6-trichloro-4-propylsulfonylpyridine, and 2,6-dichloro-3,5-dicyano-4-phenylpyridine; triazine compounds, such as 2,4-dichloro- 6-(α-chloroanilino)-s-triazine, 2-chloro-4-methylamino- 6-isopropylamino-s-triazine, 2-chloro-4,6-bis(ethylamino)-s-triazine, 2-chloro-4,6-bis(isopropylamino)-s-triazine, 2-methylthio-4,6-bis(ethylamino)-s-triazine, 2-methylthio-4-ethylamino-6-isopropylamino-s-triazine, and 2-methylthio-4-t-butylamino-6-cyclopropylamino-s-triazine; urea compounds, such as 3-(3, 4-dichlorophenyl)-1,1-dimethylurea, 3-(3,4-dichlorophenyl)- 1-methoxy-1-methylurea, 1-(α,α-dimethylbenzyl)- 3-methyl-3-phenylurea, and 1-(2-methylcyclophenyl)- 3-phenylurea; quinone compounds, such as 2-amino-3-chloro-1,4-naphthoquinone and 2,3-dicyano- 1,4-dithiaanthraquinone; N-haloalkylthio compounds, such as N-trichloromethylthiotetrahydrophthalimide, N-1,1,2,3-tetrachloroethylthiotetrahydrophthalimide, N-trichloromethylthiophthalimide, N-fluorodichloromethylthiophthalimide, N,N-dimethyl-N'-phenyl-N'-(fluorodichloromethylthio)sulfurylamide, trichloromethylthiomethanesulfone-p-chloroanilide, N-(1,1,2,2-tetrachloro-2-fluoroethylthio)methanesulfonanilide, N-fluorodichloromethylthio-N- 3-chlorophenyl-N'-dimethylurea, N-fluorodichloromethylthio-N- 3,4-dichlorophenyl-N'-methylurea, and N-fluorodichloromethylthio-N-trissulfonyl-N-methylamine; maleimide compounds, such as N-(2-chlorophenyl)maleimide, N-(4-fluorophenyl)maleimide, N-(3,5-dichlorophenyl)maleimide, N-(2,4,6-trichlorophenyl)maleimide, N-4-tolylmaleimide, and N-2,4-xylylmaleimide; thiadiazine compounds, such as 3,5-dimethyltetrahydro- 1,3,5,2(H)-thiadiazin-2-one, 3,3'-ethylenebis(tetrahydro- 4,6-dimethyl-2(H)-1,3,5-thiadiazin-2-one, 3,5-dimethyl-2-thiotetrahydro-1,3,5-thiadiazine, and 3,5-dibenzyltetrahydro-1,3,5-thiadiazin-2-thione; thiocyanogen compounds, such as methyl thiocyanide, chloromethyl thiocyanide, ethyl thiocyanide, methylenebisthiocyanate, chloromethylenebisthiocyanate, ethylenebisthiocyanate, chloroethylenebisthiocyanate, isobornyl thiocyanacetate, methyl isothiocyanate, allyl isothiocyanate, phenyl isothiocyanate, and benzyl isothiocyanate; alkylphenol compounds, such as caprylphenol and nonylphenol; alkylphenyl phosphite compounds, such as tris(octylphenyl) phosphite, tris (nonylphenyl) phosphite, tris(dinonylphenyl) phosphite, and tris (mono/di-mixed nonylphenyl) phosphite; and alkylphenyl phosphate compounds, such as tris (octylphenyl) phosphate, tris(nonylphenyl) phosphate, tris(dinonylphenyl) phosphate, and tris(mono/di-mixed nonylphenyl) phosphate.

The antifouling agent according to the present invention is used usually as formulated into an antifouling coating composition or an antifouling solution for fishing nets, etc. The content of the polysulfide compound of formula (I) preferably ranges from 0.5 to 90% by weight, still preferably from 5 to 80% by weight, and is appropriately selected from this range taking the purpose of application and the expected duration of the antifouling effects into consideration. For example, the compound of formula (I) may be formulated into an about 80% by weight solution, which is suitably applied to fishing nets by immersion or coating. It may also be incorporated into a coating and applied to ships or submerged structures as an anti-fouling coating.

Other components which can be used in the preparation of the above-mentioned antifouling coatings or solutions are not particularly restricted, and any components conventionally employed for preparing coatings or solutions of this kind may be used as such. For example, suitable resin vehicles to be used in organic solvent type coatings include vinyl chloride resins, chlorinated rubber resins, chlorinated polyethylene resins, chlorinated polypropylene resins, acrylic resins, styrene-butadiene resins, polyester resins, epoxy resins, polyamide resins, petroleum resins, silicone resins, silicone rubber resins, wax, paraffin, rosin esters, and rosin resins, and mixtures of two or more thereof. Suitable resin vehicles to be used in water-based coatings include acrylic emulsion resins, epoxy emulsion resins, and vinyl acetate resins.

If desired, the antifouling agent of the present invention may contain conventionally employed additives, such as plasticizers, pigments, fillers, solvents, and the like at an arbitrary ratio.

The present invention will now be illustrated in greater detail with reference to the following Examples, but it should be understood that the present invention is not construed as being limited thereto. All the parts and percents are by weight unless otherwise indicated.

EXAMPLE 1

Twenty parts of a test compound were added to 100 parts of a 30% xylene solution of chlorinated rubber having a chlorine content of 65% (CR-20, produced by Asahi Denka Kogyo K.K). After thoroughly stirring, the mixture was applied onto a hard vinyl chloride plate and dried for 24 hours to prepare a test piece.

The test piece was set on a raft for aquaculture and immersed in sea water at the depth of 1 m off the coast of Yokosuka, Kanagawa, Japan. The degree of fouling due to adhesion of aquatic pests was observed with time to obtain a ratio of the adhesion area to the total coated area, which was graded A to D according to the following standard. The results obtained are shown in Table 1.

Standard of Evaluation:

A . . . No adhesion

B . . . Adhesion to area of 50% or less

C . . . Adhesion to area exceeding 50%

D . . . Adhesion to all over the coated area (the coated area completely covered with pests)

TABLE 1

| Run No. | Test Compound | After 1 Month | After 3 Months | After 6 Months |
| --- | --- | --- | --- | --- |
| Ex. | | | | |
| 1-1 | Compound 1 | A | A | A |
| 1-2 | Compound 2 | A | A | A |
| 1-3 | Compound 3 | A | A | A |
| 1-4 | Compound 4 | A | A | B |
| 1-5 | Compound 5 | A | A | B |
| 1-6 | Compound 6 | A | A | A |
| 1-7 | Compound 7 | A | A | B |
| 1-8 | Compound 8 | A | A | B |
| 1-9 | Compound 9 | A | A | A |
| 1-10 | Compound 10 | A | A | B |
| 1-11 | Compound 11 | A | A | B |
| 1-12 | Compound 12 | A | A | B |
| 1-13 | Compound 13 | A | A | B |
| 1-14 | Compound 14 | A | A | B |
| Comp. Ex. | | | | |
| 1-1 | none | B | D | D |
| 1-2 | di-t-nonyl disulfide | B | D | D |
| 1-3 | tetraethylthiuram disulfide | A | C | D |
| 1-4 | copper suboxide | A | B | C |

EXAMPLE 2

| Formulation | (wt %) |
| --- | --- |
| Test compound (see Table 2) | 10 |
| Acrylic resin (50% xylene solution)* | 20 |
| Chlorinated paraffin** | 1 |
| Xylene | 69 |

*: NT-100, produced by Nitto Kasei K.K.
**: ADEKA CIZER E-430, produced by ASAHI DENKA KOGYO KABUSHIKI KAISHA The above components were thoroughly mixed in a high-speed homomixer to prepare an antifouling agent for fishing nets.

A polyethylene-made knotless net (60 strands-twisted, 20 cm×30 cm) was soaked in the antifouling agent and dried in air for 2 days. The antifouling effect of the thus treated fishing net was evaluated in the same manner as in Example 1. The results obtained are shown in Table 2.

TABLE 2

| Run No. | Test Compound | After 1 Month | After 3 Months | After 6 Months |
|---|---|---|---|---|
| Ex. | | | | |
| 2-1 | Compound 1 | A | A | B |
| 2-2 | Compound 2 | A | A | A |
| 2-3 | Compound 3 | A | A | A |
| 2-4 | Compound 4 | A | A | B |
| 2-5 | Compound 5 | A | B | C |
| 2-6 | Compound 6 | A | B | B |
| 2-7 | Compound 7 | A | B | B |
| 2-8 | Compound 8 | A | B | C |
| 2-9 | Compound 9 | A | A | B |
| 2-10 | Compound 10 | A | A | B |
| 2-11 | Compound 11 | A | B | B |
| 2-12 | Compound 12 | A | A | B |
| 2-13 | Compound 13 | A | B | B |
| 2-14 | Compound 14 | A | A | B |
| Comp. Ex. | | | | |
| 2-1 | none | B | D | D |
| 2-2 | di-t-nonyl disulfide | B | D | D |
| 2-3 | tetraethylthiuram disulfide | A | D | D |
| 2-4 | copper suboxide | A | C | D |

From the results of the foregoing Examples, it is apparent that a dialkyl polysulfide compound produces no antifouling effect at all, and other sulfur-containing compounds, typically thiuram compounds, are of short duration, while the effects of the specific disulfide compounds according to the present invention are sustained for a prolonged period of time.

Believed to have no such adverse influences upon the ecosystem as toxicity and teratogenicity, the specific disulfide compounds of the present invention are highly useful as an antifouling agent for use in water causing no environmental pollution.

While the invention has been described in detail and with reference to specific examples thereof, it will be apparent to one skilled in the art that various changes and modifications can be made therein without departing from the spirit and scope thereof.

What is claimed is:

1. An antifouling agent containing a carrier, and, as an active ingredient, an effective amount of one or more compounds represented by formula (I):

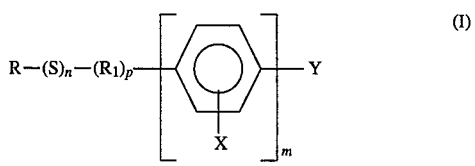

wherein R represents an alkyl group; $R_1$ represents an alkylene group; n represents an integer of 2 to 5; m and p each represent 0 or 1; X represents a nitro group, an alkyl group, an alkoxy group, a halogen atom or a hydrogen atom; and Y represents a nitro group or a halogen atom; provided that the sum of m and p is 1 or 2, said amount being effective to prevent fouling of a submerged structure to which said agent is applied.

2. An antifouling agent as claimed in claim 1, wherein R is an alkyl group having 6 to 18 carbon atoms.

3. An antifouling agent as claimed in claim 2, wherein R is a straight-chain alkyl group.

4. An antifouling agent as claimed in claim 1, wherein $R_1$ is an alkylene group having 1 to 4 carbon atoms.

5. An antifouling agent as claimed in claim 4, wherein $R_1$ is a methylene group.

6. An antifouling agent as claimed in claim 1, wherein n is 2.

7. An antifouling agent as claimed in claim 1, wherein m is 0.

8. An antifouling agent as claimed in claim 1, wherein Y is a halogen atom.

9. An antifouling agent as claimed in claim 8, wherein Y is a chlorine atom.

10. An antifouling agent as claimed in claim 1, wherein said compound represented by formula (I) is an alkylchloromethyl disulfide compound.

11. An antifouling coating composition containing a resin vehicle and an effective amount of one or more compounds represented by formula (I):

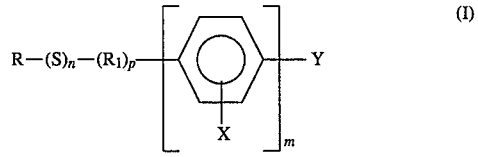

wherein R represents an alkyl group; $R_1$ represents an alkylene group; n represents an integer of 2 to 5; m and p each represent 0 or 1; X represents a nitro group, an alkyl group, an alkoxy group, a halogen atom or a hydrogen atom; and Y represents a nitro group or a halogen atom; provided that the sum of m and p is 1 or 2, said amount being effective to prevent fouling of a submerged structure to which said coating composition is applied.

12. An antifouling coating composition as claimed in claim 11, wherein said effective amount ranges from 0.5 to 90% by weight.

13. An antifouling coating composition as claimed in claim 11, wherein said resin vehicle is chlorinated rubber.

14. An antifouling coating composition as claimed in claim 11, wherein said resin vehicle is an acrylic resin.

* * * * *